(12) United States Patent
Kim

(10) Patent No.: US 11,400,182 B2
(45) Date of Patent: Aug. 2, 2022

(54) INJECTABLE FORMULATION CONTAINING A POLY L LACTIC ACID FILLER AND A HYALURONIC ACID FILLER CONJUGATE AND A METHOD FOR PREPARING THE SAME

(71) Applicant: GCS Co., Ltd., Seongnam-si (KR)

(72) Inventor: Chang Sik Kim, Suwon-si (KR)

(73) Assignee: GCS Co., Ltd., Seongnam-si (KR)

( * ) Notice: Subject to any disclaimer, the term of this patent is extended or adjusted under 35 U.S.C. 154(b) by 19 days.

(21) Appl. No.: 17/057,781

(22) PCT Filed: Nov. 6, 2020

(86) PCT No.: PCT/KR2020/015505
§ 371 (c)(1),
(2) Date: Nov. 23, 2020

(87) PCT Pub. No.: WO2021/101139
PCT Pub. Date: May 27, 2021

(65) Prior Publication Data
US 2021/0379244 A1 Dec. 9, 2021

(30) Foreign Application Priority Data

Nov. 22, 2019 (KR) ........................ 10-2019-0151389

(51) Int. Cl.
*A61L 27/26* (2006.01)
(52) U.S. Cl.
CPC ......... *A61L 27/26* (2013.01); *A61L 2300/622* (2013.01); *A61L 2430/34* (2013.01)
(58) Field of Classification Search
None
See application file for complete search history.

(56) References Cited

U.S. PATENT DOCUMENTS

2015/0366976 A1   12/2015   Nguyen et al.

FOREIGN PATENT DOCUMENTS

| CN | 105879124 A | 8/2016 |
| EP | 3730161 A1 | 10/2020 |
| JP | 2014521492 A | 8/2014 |
| KR | 101706254 B1 | 2/2017 |
| KR | 1020170116465 A | 10/2017 |
| KR | 101852127 B1 | 4/2018 |
| KR | 101854540 B1 | 6/2018 |
| KR | 1020180130344 A | 12/2018 |
| RU | 2017119805 A3 | 6/2019 |
| WO | 2009018546 A1 | 2/2009 |
| WO | 2013071216 A1 | 5/2013 |

OTHER PUBLICATIONS

ISR issued in corresponding Patent Application No. PCT/KR2020/015505, dated Feb. 15, 2021.
Search Report issued in Russian Patent Application No. 2021121215, dated Dec. 10, 2021.
Office Action issued in Russian Patent Application No. 2021121215, dated Dec. 17, 2021.
EESR issued in corresponding European Patent Application No. 20806918.7, dated Apr. 5, 2022.

*Primary Examiner* — Robert A Wax
*Assistant Examiner* — Randeep Singh
(74) *Attorney, Agent, or Firm* — Greer Burns & Crain Ltd.

(57) ABSTRACT

Disclosed are a sustained-release injection formulation containing a biodegradable polymer microcapsule that contains a conjugate of poly-L-lactic acid (hereinafter referred to as "PLLA") filler and hyaluronic acid (hereinafter referred to as "HA") and contains a PLLA-HA microcapsule, and a method of preparing the same.

4 Claims, No Drawings

INJECTABLE FORMULATION CONTAINING A POLY L LACTIC ACID FILLER AND A HYALURONIC ACID FILLER CONJUGATE AND A METHOD FOR PREPARING THE SAME

This is a National Phase Application filed under 35 U.S.C. § 371 of International Application No. PCT/KR2020/015505, filed Nov. 6, 2020, which claims benefit of Korean Patent Application 10-2019-0151389 filed Nov. 22, 2019, the contents of which are incorporated herein by reference.

TECHNICAL FIELD

The present invention relates to an injection formulation that contains a conjugate of poly-L-lactic acid (hereinafter referred to as "PLLA") filler and hyaluronic acid (hereinafter referred to as "HA") and contains a microcapsule of PLLA-HA, and a method of preparing the same.

BACKGROUND ART

In general, a poly-L-lactic acid (PLLA) filler is a polymeric synthetic substance having biocompatibility and biodegradability as a support for microspheres. In addition, hyaluronic acid (HA) is a biosynthetic natural substance that is present in large amounts in the skin of animals and the like, and a hyaluronic acid (HA) filler is a substance used to increase facial volume without surgery.

In conventional methods of preparing and using PLLA, a mixture of PLLA as a dried powder with CMC (carboxymethyl cellulose) and mannitol is freeze-dried and the freeze-dried PLLA is mixed with distilled water to prepare a suspension, after which the prepared suspension is injected into the body. As a result, after 3 to 6 months, collagen is produced in the body to achieve a volume increase.

However, in this conventional method, there are limitations in that the distilled water component and the CMC component in the injected PLLA suspension are absorbed into the body within a few days, so the increased volume that occurred immediately after the injection of the PLLA suspension into the body disappears, the effect of increased volume cannot be obtained within a few days after the injection and can be gradually secured only after several months (3-6 months).

Therefore, a long period of several months following injection into the body is required until collagen is produced. However, this period of several months has caused dissatisfaction and complaints among subjects. Moreover, different types of fillers and biomaterials for body tissue repair should be additionally used in order to overcome this drawback, which is inconvenient.

In addition, the conventional PLLA filler has a disadvantage of causing nodules and granulomas.

In addition, PLLA is injected as a dilution with distilled water. In this case, when a suspension is prepared with distilled water, the concentration of the suspension is lowered. For this reason, there is also a problem in that a long time is required to obtain a homogeneous suspension.

In order to solve this problem, Korean Patent No. 10-1852127 discloses a method for preparing a conjugate of PLLA and HA.

However, as consumer demand for fillers is rapidly increasing and consumer requirements are becoming more detailed and concrete, there is a need for PLLA fillers having improved initial volume and suspension homogeneity compared to the prior art.

DISCLOSURE

Technical Problem

Accordingly, it is one object of the present invention to provide a conjugate of a poly-L-lactic acid (PLLA) filler and a hyaluronic acid (HA) filler, a PLLA-HA conjugate microcapsule having uniform particles, and a method of preparing the same.

Technical Solution

In accordance with the present invention, the above and other objects can be accomplished by the provision of a method for producing a filler containing a PLLA-HA microcapsule including (a) mixing PLLA (poly-L-lactic acid) with CMC (carboxymethylcellulose) and mannitol, freeze-drying the resulting mixture, pulverizing the freeze-dried product to a certain size, and sterilizing the result using gamma radiation to prepare a PLLA mixture, (b) mixing HA (hyaluronic acid) with a BDDE (butanediol diglycidyl ether) crosslinking agent, gelling the resulting mixture, washing the gel with phosphate buffer, collecting crosslinked HA with uniform particles and passing the HA through a screen to obtain crosslinked HA with uniform particles to thereby prepare a HA mixture, (c) dissolving the PLLA mixture in an organic solvent to obtain an oil phase (O), (d) adding distilled water to the crosslinked HA to obtain a water phase (W), (e) mixing the oil phase (O) with the water phase (W) to obtain a PLLA-HA emulsion, and (f) spray-drying the PLLA-HA emulsion of step (e) to prepare a microcapsule.

As used herein, the term "poly-L-lactic acid" (also called "PLLA" or "polyL-lactic acid") is a filler approved by the US FDA with regard to the treatment of facial lipid stiffness in patients infected with human immunodeficiency virus (HIV), and contains an ingredient extracted from plants such as sugarcane. In addition, hyaluronic acid (HA) is a biologically derived polymer material present widely in nature, and is a polyanionic mucopolysaccharide which was first isolated from vitreous humor of the eyes by Meyer and Palmer in 1934.

As used herein, the term "hyaluronic acid" refers to a linear polysaccharide composed of glucuronic acid and acetylglucosamine, and is a glycosamino glycan present in the extracellular matrix (ECM), the synovial fluid of the joints, and the support constituting cartilage. Hyaluronic acid also plays a critical role as a signaling molecule in cell motility, cell differentiation, wound healing and cancer metastasis. The importance thereof as a joint synovial fluid is further increased due to the particular viscoelastic properties of hyaluronic acid and crosslinked hyaluronic acid. Also, hyaluronic acid is a biomaterial having excellent biocompatibility that can be used for tissue engineering and drug delivery systems since it has no problem associated with immunity. Hyaluronic acid and hyaluronic acid oligosaccharides have a three-dimensional structure in solution and thus are capable of causing a wide range of internal hydrogen bonds, limited fluidity of polymer chains, and certain helical and coiled coil reactions.

Hyaluronic acid generally has a molecular weight of about 1,000 to 10,000,000 Da, and has certain physicochemical properties and biological functions as mentioned above.

Hyaluronic acid plays a pivotal role in the homeostasis of cellular tissues and lubrication of joints, and also plays a very important role in cell fluidity, growth factor action and inflammatory response by specifically binding to certain proteins on the cell surface. Hyaluronic acid has been developed and used as a medical component for tissue repair (replacement and reconstruction of human tissue) in Korea and other nations, and is widely used in the skin care, beauty, and plastic surgery fields.

The carboxymethylcellulose (CMC) is used as a carrier, and the carrier of the present invention is not limited to CMC, and may include at least one selected from the group consisting of carboxymethyl cellulose, sodium carboxymethyl cellulose, sodium alginate, gelatin, albumin, collagen, sodium hyaluronic acid, dextran, hydroxyethyl cellulose, hydroxypropyl methyl cellulose, glycerin, sorbitol, and propylene glycol.

In addition, the carrier herein used is mannitol, but is not limited thereto, and may be any of generally used excipients and diluents such as lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate or mineral, but is limited thereto.

The butanediol diglycidyl ether (BDDE) was used as a crosslinking agent for hyaluronic acid, but is not limited thereto, and may be selected from the group consisting of divinyl sulfone (DVS), bisethyl carbodiimide (BCDI), and polyethylene glycol (PEG).

Specifically, the freeze-drying of step (a) of the PLLA-HA microcapsule-containing filler of the present invention includes primary freeze-drying at −60 to −100° C. for 12 to 24 hours and secondary drying at 15 to 25° C. for 5 to 10 days. The size of the pulverized particles may be within the range of 30 um to 100 um, but is not limited thereto.

In addition, specifically, in the PLLA-HA-microcapsule-containing filler of the present invention, 30 to 80 liters of phosphate buffer in step (b) is used with 100 grams of HA, and uniform particles are obtained by passing the mixture through a screen with 80 to 120 mesh, but the present invention is not limited thereto.

In addition, specifically, when the PLLA-HA microcapsule-containing filler of the present invention is used as a filler for the face after step (f), 15 to 25 ml of distilled water may be mixed with 10 mg of the microcapsule, and when the PLLA-HA microcapsule-containing filler is used as a filler for the body after step (f), 25 to 35 cc of distilled water may be mixed with 10 mg of the microcapsule.

Advantageous Effects

The PLLA-HA conjugate according to the present invention is prepared using a method of preparing a microcapsule using PLGA and HA. PLLA-HA is evenly disposed in the form of an emulsion of microparticles in the suspension, thus advantageously preventing PLLA from aggregating in one place and reducing the formation of granulomas.

The effects of the present invention are not limited to those mentioned above. It should be understood that the effects of the present invention include all effects that can be inferred from the configurations described in the detailed description of the present invention or claims.

BEST MODE

A preferred embodiment of the method for preparing sustained-release microparticles containing a conjugate of a poly-L-lactic acid filler and a hyaluronic acid filler according to the present invention configured as described above will be described as follows. When it is determined that a detailed description of a related known function or configuration in the following description of the present invention may unnecessarily obscure the subject matter of the present invention, the detailed description thereof will be omitted. In addition, terms to be described later are defined in consideration of functions in the present invention, and may vary according to the intentions of users or operators, or precedents, and accordingly, the meaning of each term should be interpreted based on the contents throughout the present specification.

First, in the present invention, in order to prepare a conjugate of a poly-L-lactic acid filler (PLLA) and a hyaluronic acid filler (HA), PLLA is freeze-dried, HA is crosslinked using BDDE, and the crosslinked HA is injected into a PLLA vial, mixed, extracted with a syringe, and then used for treatment.

As used herein, the term "poly-L-lactic acid" (also called "PLLA" or "polyL-lactic acid") is a filler approved by the US FDA with regard to the treatment of facial lipid stiffness in patients infected with human immunodeficiency virus (HIV), and contains an ingredient extracted from plants such as sugarcane. In addition, hyaluronic acid (HA) is a biologically derived polymer material present widely in nature, and is a polyanionic mucopolysaccharide that was first isolated from the vitreous humor of the eyes by Meyer and Palmer in 1934.

Hyaluronic acid is distributed with various molecular weights (1 to 10 million daltons) in almost all tissues such as the skin, muscles, skeleton, blood, lymph, placenta, eyes, cartilage and synovial fluid of animals, and is most widely distributed in skin tissues among the tissues. Hyaluronic acid has been developed and used as a medical component for tissue repair (replacement and reconstruction of human tissue) in Korea and other nations, and is widely used in the skin care, beauty and plastic surgery fields.

In addition, the term "conjugate" used in the present invention means a simple mixture of a poly-L-lactic acid filler and a hyaluronic acid filler, rather than a specific type of physical or chemical combination.

Example 1. Preparation of PLLA (Poly-L-Lactic Acid) Mixture Powder

In order to prepare a PLLA mixture, first, PLLA (poly-L-lactic acid) having a molecular weight of about 150,000 kDa (kilodaltons) was prepared. CMC (carboxymethylcellulose) and mannitol were mixed with the PLLA, followed by freeze-drying. At this time, the freeze-drying was carried out by primary freeze-drying at −60 to −100° C. for 12 to 24 hours and secondary drying at 15 to 25° C. for 5 to 10 days.

The freeze-dried PLLA mixture was pulverized to a size ranging from 30 μm to 100 μm (appropriately 50 μm) using an overhead stirrer, and was subjected to gamma-ray sterilization to prepare a PLLA mixture powder.

Example 2. Preparation of O/W Emulsion

In order to prepare an emulsion of oil in water (O/W), the PLLA mixture prepared in Example 1 was stirred with a mixture of a medium chain triglyceride (MCT) oil and PGPR (polyglycerol polyricinoleate) as an emulsifier to obtain a clear oil phase (O).

The water phase (W) for encapsulating the oil phase was prepared as follows.

First, HA having a molecular weight of about 2 million kDa was mixed with BDDE (butanediol diglycidyl ether) as a crosslinking agent at a predetermined ratio, and the gelled HA was washed with a phosphate buffer. The phosphate buffer was used in an amount of 30 to 80 liters (appropriately 50 liters) with respect to 100 grams of HA.

The washed HA was passed through a screen with 80 to 120 mesh having a uniform size to obtain crosslinked HA with uniform particles. In this case, the optimal screen pore size may be 100 mesh.

Distilled water was added to the crosslinked HA and was then mixed at 9,400 rpm using a homogenizer for 5 minutes. This material was further homogenized at 14,000 rpm using a homogenizer for 5 minutes to obtain a water phase (W).

Then, the oil phase (W) was mixed with the water phase (W), followed by stirring at 400 rpm in a stirrer for 5 minutes and homogenization using a homogenizer (5 minutes, 20,000 rpm) to prepare an O/W emulsion.

Example 3. Preparation of Microcapsules Using Spray Drying

A microcapsule as a powder was prepared from the O/W emulsion prepared in Example 2 using a spray dryer (Eyela spray-dryer SD-1000, Eyela, Tokyo, Japan). Specifically, the temperature of the fed air was adjusted to 130±5° C., the discharge air temperature was adjusted to 80±5° C., the rotary sprayer was adjusted to 10×10 kPa, the blower speed was adjusted to 0.80 m$^3$/min, and the pump speed was adjusted to 1.0 mL/min.

The microcapsule prepared through the above process was injected into a vial and then gamma-ray sterilized once more and frozen at −20° C.

The present invention is characterized in that the microencapsulated PLLA-HA O/W emulsion can be used immediately after injecting injection water into the same. Specifically, when preparing a filler for the face, 15 to 25 ml of distilled water was mixed with 10 mg of the microcapsule, whereas when preparing a filler for the body, 25 to 35 cc of distilled water was mixed with 10 mg of the microcapsule.

The microencapsulated PLLA-HA O/W emulsion was completely micronized and homogenized during the preparation process, thereby solving conventional problems in which it is required to form a suspension and allow the suspension to stand for 2 hours or longer before use after mixing water for injection, and particles of PLLA agglomerate in the composition.

As described above, the present invention is characterized in that the long time taken to form initial volume during injection, which is the disadvantage of conventional PLLA filler products (e.g., products such as Sculptra), can be shortened by 6-8 weeks or more, and the present invention is based on a combination with crosslinked hyaluronic acid in order to minimize the formation of granuloma, which is another disadvantage of conventional PLLA fillers, and the aggregation of PLLA is significantly reduced even after insufficient mixing time or long-term storage by producing the same into fine particles.

The description of the present invention is provided only for illustration, and those skilled in the art will appreciate that various modifications, additions and substitutions are possible, without departing from the scope and spirit of the invention as disclosed in the accompanying claims. Therefore, it should be understood that the embodiments described above are illustrative and non-limiting in all respects. For example, a component described as a single unit may be implemented in a separated manner, and similarly, components described as being separated may also be implemented in a combined form.

The scope of the present invention is defined by the claims to be set forth below, and all alterations or modifications derived from the meanings and scopes of the claims and equivalents thereto should be construed as falling within the scope of the present invention.

The invention claimed is:

1. A method for producing a filler containing a PLLA-HA microcapsule comprising:
   (a) mixing PLLA (poly-L-lactic acid) with CMC (carboxymethylcellulose) and mannitol, freeze-drying the mixture of PLLA, CMC and mannitol, pulverizing the freeze-dried mixture, and sterilizing the pulverized freeze-dried mixture using gamma radiation to prepare a PLLA mixture;
   (b) mixing HA (hyaluronic acid) with a BDDE (butanediol diglycidyl ether) crosslinking agent to obtain crosslinked HA, gelling the mixture of HA and BDDE crosslinking agent to obtain a gel, washing the gel with a phosphate buffer, collecting the crosslinked HA and passing the crosslinked HA through a screen to obtain crosslinked HA with uniform particles;
   (c) dissolving the PLLA mixture in an organic solvent to obtain an oil phase (O);
   (d) adding distilled water to the crosslinked HA to obtain a water phase (W);
   (e) mixing the oil phase (O) with the water phase (W) to obtain a PLLA-HA emulsion; and
   (f) spray-drying the PLLA-HA emulsion of step (e) to prepare the PLLA-HA microcapsule.

2. The method according to claim 1, wherein the freeze-drying of step (a) comprises:
   primary freeze-drying at −60 to −100° C. for 12 to 24 hours; and
   secondary drying at 15 to 25° C. for 5 to 10 days, and
   wherein the pulverizing of the freeze-dried mixture results in a pulverized particle within a range of 30 μm to 100 μm.

3. The method according to claim 1, wherein the phosphate buffer in step (b) is used in an amount of 30 to 80 liters relative to 100 grams of HA, and
   the uniform particles are obtained by passing the mixture through a screen with 80 to 120 mesh.

4. The method according to claim 1, further comprising mixing 15 to 25 ml of distilled water with 10 mg of the microcapsule in order to prepare a filler for a face after step (f) and mixing 25 to 35 cc of distilled water with 10 mg of the microcapsule in order to prepare a filler for a body after step (f).

* * * * *